United States Patent [19]
Chen et al.

[11] Patent Number: 5,948,507
[45] Date of Patent: *Sep. 7, 1999

[54] ABSORBENT ARTICLES WITH REDUCED CROSS-DIRECTIONAL WRINKLES

[75] Inventors: Fung-jou Chen; Jeffrey Dean Lindsay, both of Appleton, Wis.

[73] Assignee: Kimberly-Clark Worldwide, Inc., Neenah, Wis.

[ * ] Notice: This patent is subject to a terminal disclaimer.

[21] Appl. No.: 09/114,398

[22] Filed: Jul. 13, 1998

Related U.S. Application Data

[63] Continuation of application No. 08/753,649, Nov. 27, 1996, Pat. No. 5,817,400.

[51] Int. Cl.$^6$ .............................. B32B 3/00; B29C 49/00; D21H 11/00
[52] U.S. Cl. ...................... 428/153; 428/156; 428/537.5; 428/413; 264/119; 264/167; 264/282; 264/284; 604/379; 604/380; 604/385.1; 162/109; 156/709
[58] Field of Search ..................... 428/156, 153, 428/537.5, 913, 155, 167, 141; 264/107, 282, 284; 604/379, 380, 385.1; 162/109, 214; 156/209, 196

[56] References Cited

U.S. PATENT DOCUMENTS

| | | | |
|---|---|---|---|
| 2,874,618 | 2/1959 | Yang | 428/153 |
| 4,057,669 | 11/1977 | McConnell | 428/152 |
| 4,892,535 | 1/1990 | Björnberg et al. | 604/380 |
| 5,167,897 | 12/1992 | Weber et al. | 264/288.8 |
| 5,387,385 | 2/1995 | Murji | 204/160 |
| 5,429,686 | 7/1995 | Chiu et al. | 139/383 A |
| 5,817,400 | 10/1998 | Chen et al. | 428/153 |

OTHER PUBLICATIONS

DeCrosta, Edward F., "Experimentally Determined Equations for Water Removal in the Press Section: Suction Box De–watering," *Tappi Journal,* vol. 56, No. 11, Nov. 1973, pp. 100–106.

Wrist, P. E., "The Present State of Our Knowledge of the Fundamentals of Wet Pressing," *Pulp and Paper Magazine of Canada,* vol. 65, No. 7, Jul. 1964, pp. T284–T296.

Yih, Chia–Shun and S. J. McNamara, "The Crushing of Wet Paper Sheets," *Tappi Journal,* vol. 46, No. 3, Mar. 1963, pp. 204–208.

*Primary Examiner*—Donald Loney
*Attorney, Agent, or Firm*—Gregory E. Croft

[57] ABSTRACT

Absorbent articles containing absorbent cores of fluff pulp frequently contain wrinkles in the absorbent core that run from side to side of the article, typically normal to the machine direction in the manufacturing process. Side-to-side wrinkles are deleterious in that they provide large flow channels for urine or other body fluids to escape to the edge of the article. Frequently, such wrinkles are present after manufacturing, before the article has been folded or worn. The cause of the wrinkles is believed to be due to natural instabilities during compression of the fluff pad shortly after it is formed. Means for reducing cross-directional wrinkles include the use of grooved, drilled, or patterned compression rolls to densify the fluff pulp while providing opportunities for reduced in-plane displacement during compression or, if in-plane displacement does occur, providing paths for cross-directional displacement as well as machine-direction displacement so that continuous CD wrinkles cannot form. The use of large diameter rolls with soft rubber covers can also be used.

34 Claims, 2 Drawing Sheets

ABSORBENT ARTICLES WITH REDUCED CROSS-DIRECTIONAL WRINKLES

This application is a continuation of application Ser. No. 08/753,649, now U.S. Pat. No. 5,817,400 entitled ABSORBENT ARTICLES WITH REDUCED CROSS-DIRECTIONAL WRINKLES and filed in the U.S. Patent and Trademark Office on Nov. 27, 1996. The entirety of application Ser. No. 08/753,649 is hereby incorporated by reference.

BACKGROUND OF THE INVENTION

Absorbent articles containing absorbent cores of fluff pulp frequently contain wrinkles in the absorbent core that run from side to side of the article, typically normal to the machine direction in the manufacturing process. Side-to-side wrinkles are deleterious in that they provide large flow channels for urine or other body fluids to escape to the edge of the article. Frequently, such wrinkles are present after manufacturing, before the article has been folded or worn.

Among those working in the art of absorbent article manufacture, several theories have been proffered for the cause of fluff wrinkles. It is sometimes assumed that the wrinkles are the result of unavoidable in-plane compression as tension in the adjoining webs is released. For example, the forming tissue is the layer of creped tissue paper on which the loose fluff pulp pad is deposited in an air-laying process. Tension exists in the forming tissue as it is carried on rolls and between nips, and some tension may be needed for processing. The fluff pad is thus formed on a tissue that is under tension and has been stretched. When the tension is relieved later in the process, the tissue contracts and may cause the fluff pad to contract also, perhaps causing some disruption of the fluff pad. In-plane disruption from stress relaxation may also occur when a topsheet is combined with the fluff pad superposed on a bottom sheet, for the topsheet may be under tension (as well as the bottomsheet or forming tissue) which will be released after it has been attached to fluff. This mechanism has been suggested as the cause of wrinkles in the absorbent core. For example, Weber et al. in U.S. Pat. No. 5,167,897, "Method For Incrementally Stretching A Zero Strain Stretch Laminate Web To Impart Elasticity Thereto," issued Dec. 1, 1992, teach that continuous webs of backsheet material and topsheet material, which are combined with an absorbent core, "are preferably maintained under very slight (essentially 'zero strain') tension in the machine direction to prevent wrinkling and to facilitate registration with the diaper assembly and converting operations until the completed diaper web is severed into discrete diapers." The implication is that strain in webs attached to the absorbent core will cause wrinkling of the core.

Some have assumed that the wrinkles are a result of general and unavoidable in-plane stresses during handling of the fluff pad, particularly during folding and packaging operations.

In examining the physical nature of regular cross-direction wrinkles in commercial diapers, viewing of the fluff pad against strong light from behind allows one to see that most wrinkles occur in zones of low basis weight, as if the pad had been seriously disrupted at that point. Mere folding of the absorbent core in areas of uniform basis weight does not result in low basis weight zones, as is easily verified experimentally. Bending or folding an unwrinkled, uniform region of a pad of fluff pulp constrained between tissues does not result in the types of low basis weight wrinkled areas seen in manufactured articles. Wrinkles are more likely to form during folding in those zones where the pad has been disrupted and has locally low basis weight and thus low stiffness, but the folding is not the cause of the basis weight disruption. Even after the diaper is unfolded and flattened out, apparent wrinkles or regions of low basis weight are evident. These wrinkles are signs of in-plane disruption that occurred during manufacturing. The wrinkles associated with low basis weight zones may compromise pad integrity during use, provide channels for leakage to the side, and disrupt the continuity of the fibrous network and thus interfere with wicking.

While high tension in adjoining webs may impart wrinkling to a fluff pad when the tension is relieved, such wrinkles would primarily be zones of locally increased basis weight as the fibrous web was contracted. In contrast, the wrinkles that are viewed as most harmful to diaper performance are associated with low basis weight regions. Neither relaxation of adjoining web tension nor folding of the diaper during packaging can account for the nature of the most harmful form of wrinkles associated with low basis weight zones. Surprisingly, serious investigations into the cause of wrinkles in the absorbent core appear to have been neglected in prior art, in spite of the long-felt need for absorbent articles that are less subject to leaks. Even though wrinkles are visible in products, previous analysis of leakage and absorbency of diapers and related articles has typically assumed that the absorbent core is a homogenous, wrinkle-free, non-disrupted fluff pad with uniform basis weight and continuous wicking paths for fluid. The invalidity of such assumptions due to the presence of macroscopic wrinkles may partly account for continued high levels of leakage problems in many apparently advanced, highly engineered absorbent articles. Accordingly, an object of the present invention is to provide a means for processing air-laid fluff pulp pads for use in absorbent cores which reduces the number of wrinkles in the core. A further object is to improve core integrity by reduction of disrupted regions of low basis weight running in the cross direction of the core. A further object is to improve longitudinal wicking of an absorbent core by reducing the number of discontinuities in the fibrous medium that could block or disrupt flow of fluids along the length of the core. Yet another object is to provide means for allowing increased production speed of diaper machines and other production devices for absorbent articles such that pad integrity and wicking continuity is not sacrificed at the elevated speed by in-plane disruption of the absorbent core during compressive events.

SUMMARY OF THE INVENTION

Based on observations, it is now believed that an important cause of wrinkles in absorbent cores is the result of a compression instability that occurs during compression of the fluff pad shortly after it is formed. Compression of the pulp by a roll can lead to disruption of the weak fluff structure in a manner analogous to the problem of crushing in the pressing of wet paper, wherein compressed water is unable to escape into an underlying felt rapidly enough as the sheet is being compressed and causes in-plane disruption of the sheet as it flows back out of the nip. In the case of absorbent core compression, the core entering a nip experiences wedge-like forces extending both downward and away from the nip. At high speed, the in-plane or shear forces of the pad entering then nip may exceed the strength of the web and cause periodic elements of the core to be pushed back, resulting in local disruption of the web and a narrow region of lower basis weight where the pad has been torn, in effect. The problem of in-plane disruption may be avoided at low speeds or in hand assembly of diapers, but may be particularly challenging for mass production.

A feature often observed in the low basis weight wrinkles is that they tend to be curved, having "smile" shapes. This is consistent with a crush-like mechanism due high in-plane stresses during compression. At the edges of the absorbent core, in-plane stresses can be relieved by expansion toward the side, in the cross direction. In the center of the absorbent core, the restraint of the surrounding material forces the direction of in-plane shifting to be in the negative machine direction. With reduced ability for stress relief by cross-direction shifting of the pad, sheet disruption is most likely to begin in the center of the absorbent core, with a tear line then spreading out to the sides as the core continues moving into the nip. Thus, a smile-like profile may be expected in many cases, depending on the details of absorbent core width, and compression roll width and speed.

In order to reduce the occurrence of cross-directional wrinkles, softer, longer nips and grooved or patterned rolls can be used such that backward (negative machine direction) disruptive forces are reduced and better pad restraint is provided. More specifically, grooved, drilled, or patterned compression rolls can be used to densify the fluff pulp while providing opportunities for reduced in-plane displacement during compression or, if in-plane displacement does occur, to provide paths for cross-directional displacement as well as machine-direction displacement so that continuous CD wrinkles cannot form. Compression rolls with staggered bilateral arrays of protuberances are especially preferred. Large diameter rolls with soft rubber covers can also be used. In one embodiment of the invention, the fluff pad can be restrained in place during compression through the use of a highly textured web which makes contact with the fluff pulp prior to or during compression and effectively engages the fluff pad to prevent significant in-plane shifting during compression.

Hence in one aspect, the invention resides in a method for preparing absorbent articles comprising the steps of: a) depositing comminuted fibers onto a forming surface to form a bulky mat having a thickness of at least 2 mm; b) reducing the thickness of said mat by at least 10% using a nonuniform compression roll; and c) incorporating said mat into an absorbent article to serve as an absorbent core.

In another aspect, the invention resides in a method for preparing absorbent articles comprising the steps of: a) depositing comminuted fibers and up to 90% by weight of superabsorbent particles onto a forming surface to form a bulky mat having a thickness greater than 2 mm; b) reducing the thickness of said mat by at least 10% using a soft, deformable compression roll having an effective nip width of at least 1 inch; and c) incorporating said mat into an absorbent article to serve as an absorbent core.

In another aspect, the invention resides in a method for mass producing absorbent articles at high speed comprising the steps of: a) depositing comminuted fibers onto a forming surface to form a fluff pad having a thickness of at least 2 mm; b) placing a textured web in contact with said fluff pad, said textured web having elevated structural elements suitable for engaging and restraining said fluff pad during compression; c) reducing the thickness of said mat by at least 10% while in contact with said textured web; and d) incorporating said mat into an absorbent article to serve as an absorbent core.

In another aspect, the invention resides in a method for mass producing absorbent articles at high speed comprising the steps of: a) depositing comminuted fibers onto a forming surface to form a fluff pad having a thickness of at least 2 mm, said forming surface comprising a textured web having elevated structural elements suitable for engaging and restraining said fluff pad during compression; b) reducing the thickness of said mat by at least 10% while in contact with said textured web; and c) incorporating said mat into an absorbent article to serve as an absorbent core.

In another aspect, the invention resides in an absorbent article having an air-laid absorbent core comprising a fluff pulp pad, said pad having a longitudinal direction tensile strength to cross direction tensile strength ratio of at least 1.0 and a repeating pattern of spaced apart densified regions therein, said regions having a CD:MD In-plane Disruption Ratio (hereinafter defined) of 1 or greater.

The textured surfaces of the compression rolls comprise depressions or preferably protuberances having CD:MD In-plane Disruption Ratios greater than about 1, more specifically greater than about 2, more specifically greater than about 5, still more specifically greater than about 10, and still more specifically from about 5 to about 25. In one embodiment, surface elements on the compression roll have at least one characteristic length scale (the major or minor axis, for example, of an approximately elliptical or rectangular structure) of from about 1 to about 50 mm, more specifically from about 2 to about 30 mm, more specifically from about 3 to about 25 mm, and most specifically from about 8 to about 15 mm.

An alternative embodiment modifies the compression nip to increase nip width and reduce backward wedge-like forces by using a soft rubber-like compression roll cover or a compression roll capable of deforming to give an effective nip width of at least about 1 inch or greater, more specifically 2 inches or greater, more specifically 3 inches or greater, and still more specifically from about 1 inch to about 4 inches when loaded against an incompressible surface at the load to be used during processing of the fluff pad. The roll should have a Durometer hardness of about 60 or less, more specifically of about 40 or less, more specifically about 30 or less, still more specifically about 20 or less, and still more specifically from about 10 to about 60.

DEFINITIONS OF TERMS

The "thickness" of a fluff pad refers to thickness measured with a platen-based thickness gauge at a load of 0.05 psi.

A "fluff pad" is a mat containing at least 10% by weight of air-laid, comminuted fibers, with the remainder of the mass comprising superabsorbent particles, fillers, deodorants, and other materials known in the art.

The "CD:MD In-plane Disruption Ratio" is the length of the perimeter of a raised or lowered structural element on a compression surface when the perimeter is projected in the cross direction divided by the length of the perimeter when projected in the machine direction. The CD:MD In-plane Disruption Ratio is described in more detail below.

The "effective nip width" is the contact length in the machine direction of a deformable compression roll when loaded against an incompressible surface at the load to be used during processing of a fluff pad.

The "MD:CD tensile ratio" is the ratio of tensile strength of the air-laid absorbent fluff pad removed from adjoining webs measured on a 2-inch wide specimen with an Instron tensile tester with a crosshead speed of 10 inches per minute. Specimens are conditioned under Tappi conditions (73° F., 50% relative humidity) for 24 hours. The span between the jaws should be 2 inches for the CD tensile measurement and 4 inches for the MD tensile measurement. An average is taken of 10 measurements on different samples to obtain average CD and MD tensile strengths, then the ratio of average MD to average CD tensile strength is taken.

DETAILED DESCRIPTION OF THE DRAWINGS

Figure 1:
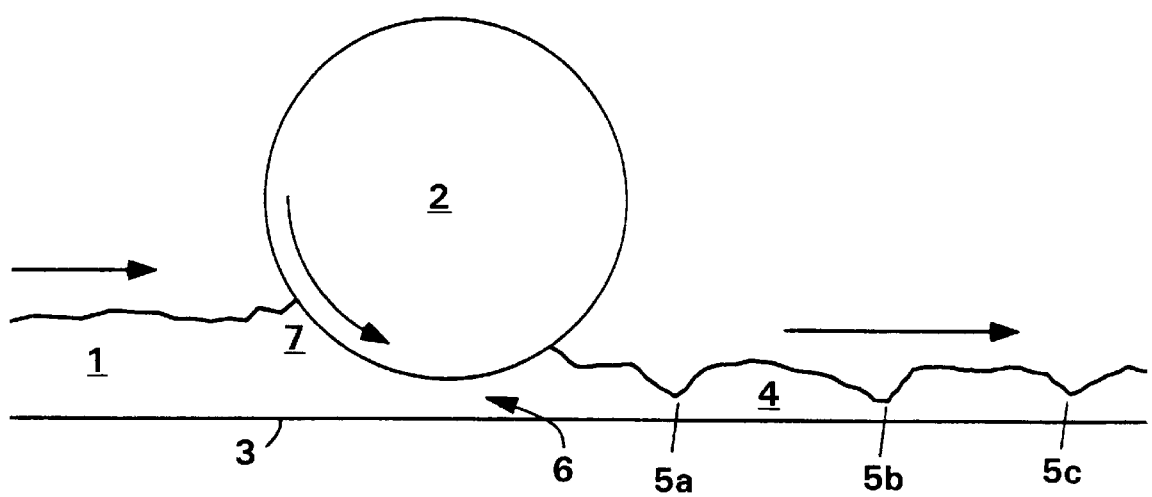
FIG. 1 is a schematic of a continuous air-laid fluff pad being compressed in a manner which results in web disruption.

Referring to the conventional process in FIG. 1, a continuous air-laid fluff pad 1 is formed on a forming tissue 3, undergoing compression by a rotating compression roll 2. The fluff pad may comprise superabsorbent particles and other materials known in the art, but should contain at least 10% by weight of absorbent fibers and preferably at least 25% of natural absorbent fibers such as wood pulp or the like. Typically, the fluff pad will have a thickness greater than about 2 mm, more typically greater than 4 mm, and more typically still greater than 8 mm and less than 40 mm. After passing through the nip 6, the thickness of the fluff pad 4 will be reduced by at least 10%, typically at least 20%, and more typically at least 30%. Some of the fluff pulp may occasionally fail momentarily to enter the nip 6, being driven back by a wedge-like force acting counter to the machine direction, resulting in momentary buildup 7 of fluff pulp before the nip while the pad continues to be strained in the machine direction. As a result, regions of low basis weight such as 5a, 5b, and 5c are formed from the disruption and partial tearing of the web.

Figure 2:
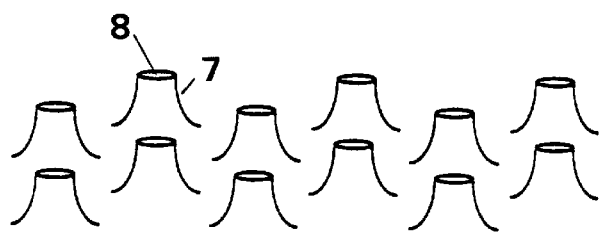
FIG. 2 depicts raised surface projections on a compression roll designed to prevent wrinkling of the absorbent core.
Figure 3:
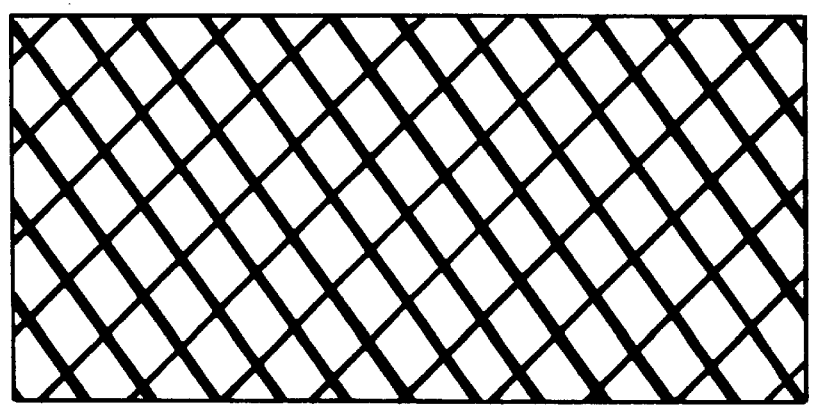
FIG. 3 depicts a pattern of grooves engraved in the surface of a compression roll to prevent wrinkling of the absorbent core.

To prevent instabilities in the movement of an absorbent core web through a compression nip, the compressing surface of roll 2 should have characteristics necessary to stably feed fluff through the nip while reducing the likelihood of web disruption in the machine direction. One means is to use a roughened surface on the compression nip roll 2 to better engage the fluff pad and force it through the nip. The surface may be roughened by engraving or cutting grooves or other depressions in the surface, such that much of the surface is smooth, interrupted occasionally with depressions. Alternatively, in a preferred embodiment of the invention, a dominantly smooth roll surface is interrupted by raised protuberances that can engage the fluff pad. Such protuberances may be arranged in a bilaterally staggered array or a random grid to more evenly distribute compression points. FIG. 2 provides an example of raised projections 7 rising from a smooth surface (not shown). The projections terminate in a substantially flat upper surface 8. FIG. 3 is an example of a groove pattern that could be engraved, cut, or formed into a roll surface to better engage fluff pulp during compression and to provide space for preferential sideways (cross direction) expansion or shifting of fibers during compression.

Whether the textured compression roll has depression or protuberances, the shape and orientation of such fluff-engaging elements can have an important effect on pad integrity and uniformity. Differential compression will occur around the perimeter of a depression or protuberance, which approximately marks the boundary between more and less highly compressed zones of the fluff. Compressed fluff, under some conditions, may shift laterally toward less compressed regions. It is preferable to orient the preferred direction of in-plane shifting to be as much in the cross-direction as possible to prevent cross machine-direction wrinkles and bands of poor integrity. This can be achieved by having differential surface elements oriented primarily in the machine direction such that fiber rearrangement, which at a local level will likely occur largely normal to the tangent of the perimeter, will be preferentially in the cross-direction if it occurs at all.

The degree to which raised or lowered surface elements on a compression roll are believed to promote CD rather than MD disruption is tied to a geometric factor defined as the CD:MD In-plane Disruption Ratio. For a single differential element on a compression roll, the CD:MD In-plane Disruption Ratio is the ratio of the length of the perimeter of the element when the perimeter is projected in the cross direction to the length of the perimeter when projected in the machine direction. If the CD:MD In-plane Disruption Ratio is greater than about 1, then in-plane shifting of fluff pulp compressed by a compression roll fluff pulp will likely be preferentially in the cross machine direction.

Figure 4:
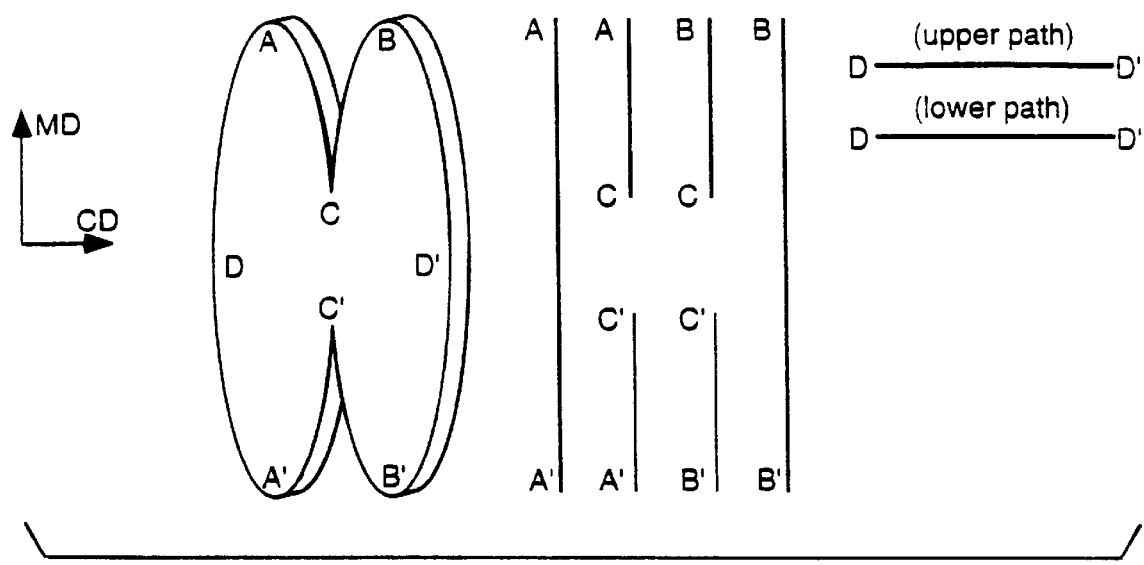
FIG. 4 depicts a hypothetical raised surface element for a compression roll and shows projected perimeter lengths in the cross-direction and machine-direction to illustrate the calculation of CD:MD In-plane Disruption Ratio.

FIG. 4 depicts a raised element consisting of two overlapping elliptical regions, for which the CD:MD In-plane Disruption Ratio will be described by way of example. The perimeter is discretized between points labeled A, A', B, etc. The cross machine-direction projection of the perimeter between points A and A' is given by the straight vertical line to the right of the raised element (A–A'). Likewise the cross machine-direction projections of the remaining segments of the perimeter are shown. Taking the shortest line segments (A–C, B–C, A'–C', and B'–C') as each having a unit length of one, then the longer lines (A–A' and B–B') have a length of about 2.6. Therefore, the total cross machine-direction projected perimeter length is 9.2 (4*1 +2*2.6). The machine-direction projection of the perimeter is done for the upper and lower halves of the raised element between points D and D'. Each pathway gives a projection of the length shown at the rightmost side of FIG. 4 (two horizontal lines), said length being about 1.3 relative to the unit length of 1 assigned to line segment A–C. The total machine direction projection of the perimeter is then about 2.6. The ratio of the CD projected length of the perimeter to the machine direction projected length of the perimeter is 9.2/2.6, or about 3.5. Therefore, the CD:MD In-plane Disruption Ratio of the raised element is about 3.5, indicating that in-plane disruption during compression may be more likely to occur in the cross direction than in the machine direction. The CD:MD In-plane Disruption Ratio is only one of several factors which will determine how and where in-plane disruption may occur, but is useful to characterize preferred geometrical structures for textured or patterned rolls. For textured compression rolls, preferred embodiments have depressions or more preferably protuberances having CD:MD In-plane Disruption Ratios of about 1 or greater, preferably about 2 or greater, more preferably about 5 or greater, and most preferably about 10 or greater, and more specifically from about 5 to about 25.

When surface structural elements on the roll comprise repeating elements, then only one element needs to be considered, otherwise an area-weighted average of different elements should be used, based on the upper surface area of the raised elements.

Grooves on the compression roll may run in the machine direction, but the compression zones of the pad would then be in a constant location that might lead to runnability problems such as excessive wear on underlying pad support elements in the nip. A spiral-like groove pattern may be preferably, for the position of the compression zones will continually shift from side to side. Accordingly, grooves predominantly in the machine direction may be advantageously turned from the machine direction at an angle of at least about 5 degrees and preferably at least about 10 degrees to yield a spiral path or a series of angled loops about the roll. Nonparallel sets of grooves can be used, such as the two sets shown in FIG. 3. At least one set of grooves should be oriented within 45 degrees and preferably within 30 degrees of the machine direction.

Drilled holes, and preferably blind drilled holes, can be used instead of grooves.

Structural elements on the surface, such as grooves or protuberances, should have at least one in-plane length scale (e.g., width or length but not height) on the order of a characteristic floc size in the air laid pad for best engagement and handling of the fluff pad. The length scale of a structural element could be the width of a groove, the land space between grooves, the diameter of a circular protuberance, or the minor or major axis of an elliptical or rectangular element. Typical floc sizes will be on the order of a fiber length or greater. For typical wood fibers, the characteristic floc size may be taken as being between 1 and 50 mm, typically between 2 and 30 mm, more typically between 3 and 25 mm, and most typically between 8 and 15 mm.

In one embodiment, structural elements have a characteristic height or depth preferably in the range of about 0.1 to 10 mm, more preferably in the range of about 0.2 to 10 mm, more preferably still at least 0.5 mm, and most preferably in the range of about 1 to 5 mm.

An alternative embodiment modifies the compression nip to increase nip width and reduce backward wedge-like forces by using a soft rubber-like compression roll cover or a compression roll capable of deforming to give an effective nip width of at least 1 inch, preferably 2 inches, and most preferably at least 3 inches when loaded against an incompressible surface at the load to be used during processing of the fluff pad. The roll should have a Durometer Shore-A hardness of less than 60, preferably less than 40, more preferably less than 30, and most preferably less than 20. The deformable roll preferably is grooved or provided with structural elements of the kind recited above for a textured roll.

Using the above methods of the present invention, the compressed fluff pad should be largely free of low basis weight wrinkles. As a result, the pad should have higher pad integrity, as measured by tensile tests. An air-laid pad should have a machine direction tensile strength approximately equal to or greater than the cross machine direction tensile strength when the pad is free of defects generated by machine-direction disruption of the pad. Accordingly, the MD:CD tensile ratio should be at least 0.5, preferably at least 0.8, more preferably at least 1, and most preferably between 1 and 3.

Figure 5:
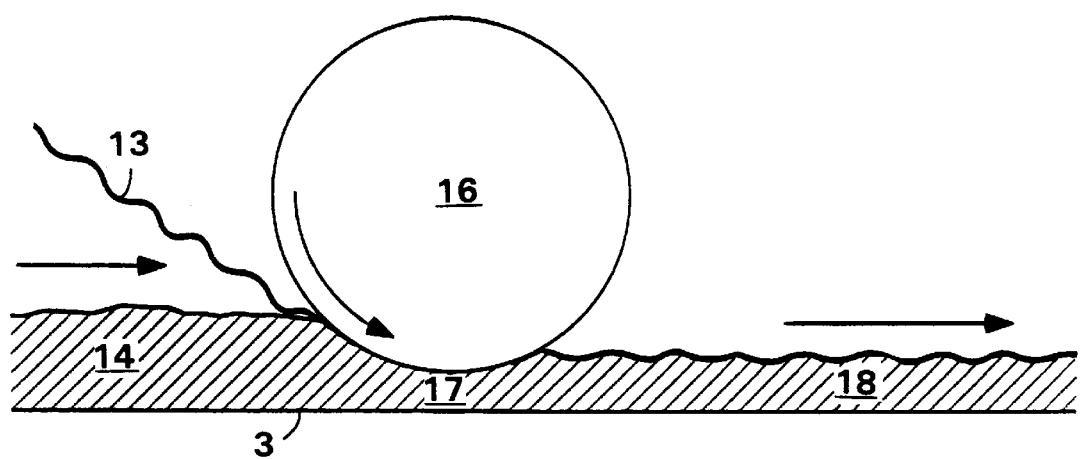
FIG. 5 depicts a highly textured topsheet being adjoined to the fluff pad during compression to engage the pad and prevent in-plane disruption.

In another preferred embodiment of the invention, the fluff pad can be restrained in place during compression through the use of a highly textured web which makes contact with the fluff pulp prior to or during compression and effectively engages the fluff pad to prevent significant in-plane shifting during compression. The highly textured web may be permanently attached to the fluff pad, serving either as a bottomsheet (e.g., a forming tissue) or a topsheet (or both, if two webs are used), or may be removed from the fluff pad subsequent to compression, in which case the textured web may be an endless loop of textured fabric or film which passes through the compression nip with the fluff pad. FIG. 5 depicts one variation of this embodiment in which a highly textured tissue web is added as a topsheet 13 to a fluff pad 14 during compression by a roll 16. The surface topography of the top sheet effectively engages the fluff pad entering the nip 17 and restrains the pad from disruptive in-plane shifting at high speed, resulting in a more uniform compressed web 18 which is expected to have good pad integrity, manifest by a high ratio of MD tensile strength to CD tensile strength and also manifest by improved longitudinal wicking across long distances. FIG. 5 is not drawn to scale. The typical texture of the incoming web may result in peak-to-valley height differences of 0.3 mm or greater.

When an adjoining web is used, it is preferred that the texture of the web accord with the previously stated principle that cross-direction shifting be more likely to occur than machine-direction shifting of the web during compression. Accordingly, the texture of the adjoining web should provide a machine-direction dominant structure, such as that accorded by elevated machine-direction strands in a woven fabric, exemplified by the novel papermaking fabric of Chiu et al. in U.S. Pat. No. 5,429,686, "Apparatus for Making Soft Tissue Products," issued Jul. 4, 1995, hereby incorporated by reference, or such as that accorded by resilient tissue webs that have been molded against such fabrics. A variety of textured web materials are feasible, including polymeric webs, woven textile fabrics, and paper webs, but it is preferred that the texture offer raised elements preferentially oriented in the machine direction, having an average CD:MD In-plane Disruption Ratio greater than about 1, preferably greater than about 2, more preferably greater than about 5, more preferably still between about 5 and 25, and most preferably greater than about 10. In a particularly preferred embodiment, the adjoining web is attached to the fluff pad as a topsheet or bottom sheet. Structural elements on the web should have a characteristic height or depth (typical peak to valley depth) preferably in the range of about 0.2 to 5 mm, more preferably in the range of about 0.3 to 3 mm, more preferably still at least 0.4 mm, and most preferably in the range of about 0.6 to 2 mm. Peak to valley depth should be measured with surface topography techniques having a z-direction resolution of about 2 microns or better and a x-y resolution (pixel size, for example) of about 70 microns by 70 microns to produce smoothing of microscopic structures, allowing consideration only of larger scale features. A suitable topography device is the CADEYES moiré interferometer, by Medar Inc. (Farmington Hills, Mich.) configured for a field of view of 38 by 38 mm with about a 500 by 500 pixel CCD camera imaging the field of view.

Web surface structures as recited above are well adapted for engaging the natural surface variations of an air-laid fluff pad for efficient control and restraint of the pad during high-speed compression. The attached topsheet or bottomsheet (or both) may additionally serve to distribute or transfer fluid to or from the absorbent core, and may also provide additional pad integrity while in use. The attached textured web may also be a composite of fibers and superabsorbent particles. The attached web may also provide novel wet resiliency and in-plane permeability properties for efficient fluid handling. The web may be apertured, slit, cut, punched, creped, or otherwise treated mechanically and chemically to enhance tactile properties, reduce stiffness in a preferred direction, and improve fluid handling abilities. The web may contain or have been reacted with deodorizing, anti-bacterial, or other chemical additives.

An absorbent article having a more uniform, high-integrity pad and a high-performance intake or distribution layer of texture, wet resilient tissue may offer excellent performance in use and be well suited as a diaper, feminine pad, breast pad, poultry pad, and the like.

It will be appreciated that the foregoing description is not to be construed as limiting the scope of this invention, which is defined by the following claims and all equivalents thereto.

We claim:

1. A mass-produced absorbent article which is substantially free of cross-direction wrinkles having an air-laid absorbent core comprising a fluff pulp pad, said pad having an MD:CD tensile ratio of at least 0.8 and a repeating pattern of spaced-apart densified regions therein, said regions having a CD:MD In-plane Disruption Ratio of 1 or greater.

2. The article of claim 1, having a CD:MD In-plane Disruption Ratio of about 2 or greater.

3. The article of claim 1, having a CD:MD In-plane Disruption Ratio of about 3 or greater.

4. The article of claim 1, having a CD:MD In-plane Disruption Ratio of about 5 or greater.

5. The article of claim 1, having a CD:MD In-plane Disruption Ratio of about 10 or greater.

6. The article of claim 1, having a CD:MD In-plane Disruption Ratio from about 5 to about 25.

7. The article of claim 1, having densified regions with a characteristic length scale from about 1 mm to about 30 mm.

8. The article of claim 1, having densified regions with a characteristic length scale from about 8 mm to about 15 mm.

9. A disposable diaper containing a compressed fluff pad which is substantially free of cross-direction wrinkles and has an MD:CD ratio of at least 0.8.

10. A mass-produced absorbent article containing a fluff pad which has been nonuniformly compressed at high speed and which is substantially free of cross-direction wrinkles and has an MD:CD tensile ratio of at least 0.8.

11. The article of claim 10, further having densified regions with a characteristic length scale from about 1 mm to about 30 mm.

12. The article of claim 10, further having densified regions with a characteristic length scale from about 8 mm to about 15 mm.

13. The article of claim 10, further having a CD:MD In-plane Disruption Ratio of about 2 or greater.

14. A method for mass producing absorbent articles comprising:
 a) depositing comminuted fibers onto a forming surface to form a bulky mat having a thickness of at least 2 mm;
 b) reducing the thickness of said mat by at least 10% to form a compressed mat without significant backward wedge-like forces acting on the bulky mat to cause in-plane disruptions of the mat, such that the compressed mat is substantially free of cross-direction wrinkles;
 c) incorporating said mat into an absorbent article to serve as an absorbent core.

15. The method of claim 14, wherein said step of reducing the thickness of the mat comprises pressing the mat in a nip with a compression roll, said nip having an effective nip width of about 1 inch or greater under normal loading without the presence of the mat.

16. The method of claim 14, wherein said effective nip width is about 2 inches or greater.

17. A method for preparing absorbent articles comprising:
 a) depositing comminuted fibers onto a forming surface to form a bulky mat having a thickness of at least 2 mm;
 b) reducing the thickness of said mat by at least 10% using a compression roll with an elongated nip having an effective nip width of about 1 inch or greater under normal loading without the presence of the bulky mat; and
 c) incorporating said mat into an absorbent article to serve as an absorbent core.

18. The method of claim 17, wherein the mat is substantially free of cross-direction wrinkles.

19. The method of claim 17, wherein the effective nip width is 2 inches or greater.

20. The method of claim 17, wherein the effective nip width is 3 inches or greater.

21. The method of claim 17, wherein the effective nip width is from about 1 inch to about 4 inches.

22. The method of claim 17, wherein said compression roll is deformable.

23. The method of claim 17, wherein said compression roll has a Durometer hardness of about 60 or less.

24. The method of claim 17, wherein said compression roll has a Durometer hardness of about 40 or less.

25. The method of claim 17, wherein said compression roll has a Durometer hardness of about 20 or less.

26. A method for mass producing absorbent articles comprising the steps of:
 a) depositing comminuted fibers onto a forming surface to form a fluff pad having a thickness of at least 2 mm;
 b) placing a textured web in contact with said fluff pad, said textured web having elevated structural elements suitable for engaging and restraining said fluff pad during compression;
 c) reducing the thickness of said mat by at least 10% while in contact with said textured web;
 d) incorporating said mat into an absorbent article to serve as an absorbent core.

27. The method of claim 26, wherein a portion of said textured web is also incorporated into said absorbent article.

28. The method of claim 26, wherein said web has a machine-direction dominant structure.

29. The method of claim 26, wherein said web comprises a material selected from a polymeric web and a woven fabric.

30. The method of claim 26, wherein said web comprises a paper web.

31. The absorbent article made according to claim 26.

32. The absorbent article of claim 26, further comprising a portion of said textured web attached to said mat.

33. A method for preparing absorbent articles comprising the steps of:
 a) depositing comminuted fibers onto a forming surface to form a bulky mat having a thickness of at least 2 mm;
 b) reducing the thickness of said mat by at least 10% using a nonuniform compression roll having a roughened surface for engaging said mat during compression; and
 c) incorporating said mat into an absorbent article to serve as an absorbent core.

34. The method of claim 33, wherein said roughened surface of said compression roll comprises random protuberances.

* * * * *